United States Patent [19]
Felix et al.

[11] Patent Number: 5,792,108
[45] Date of Patent: Aug. 11, 1998

[54] SELF-PRIMING PULSED LAVAGE PUMP

[75] Inventors: Augustus Felix, Cranston, R.I.; Donna M. Belloli, Dighton, Mass.; Dennis J. Coffey, Foster, R.I.

[73] Assignee: C. R. Bard, Inc., Murray Hill, N.J.

[21] Appl. No.: 553,772

[22] Filed: Oct. 23, 1995

[51] Int. Cl.⁶ .................................................. A61B 17/50
[52] U.S. Cl. ............................................ 604/131; 604/153
[58] Field of Search ................................. 604/152, 153, 604/154, 131, 33, 35, 39; 129/DIG. 10, DIG. 12

[56] References Cited

U.S. PATENT DOCUMENTS

| | | |
|---|---|---|
| 1,227,164 | 5/1917 | Manly . |
| 1,989,117 | 1/1935 | Svenson . |
| 2,049,524 | 7/1936 | Svenson . |
| 2,115,121 | 4/1938 | Philips . |
| 2,348,679 | 5/1944 | Groves . |
| 2,356,993 | 8/1944 | Glasner et al. . |
| 2,393,175 | 1/1946 | Laskey . |
| 2,406,115 | 8/1946 | Stephan . |
| 2,539,277 | 1/1951 | Schroepfer . |
| 2,737,896 | 3/1956 | Neyer . |
| 2,795,968 | 6/1957 | Eriksson . |
| 2,856,793 | 10/1958 | Budlong . |
| 2,921,529 | 1/1960 | Bennett . |
| 3,073,178 | 1/1963 | Barnes et al. . |
| 3,073,418 | 1/1963 | Bentley . |
| 3,119,280 | 1/1964 | Mann et al. . |
| 3,155,141 | 11/1964 | Doyle et al. . |
| 3,162,335 | 12/1964 | Kogan et al. . |
| 3,205,725 | 9/1965 | Untenwoldt . |
| 3,529,908 | 9/1970 | Smith . |
| 3,715,060 | 2/1973 | Benson . |
| 3,727,614 | 4/1973 | Kniazuk ............................ 604/152 X |
| 3,774,461 | 11/1973 | Smith ............................... 74/49 |
| 4,047,851 | 9/1977 | Bender ............................. 417/412 |
| 4,126,132 | 11/1978 | Portner et al. . |
| 4,225,061 | 9/1980 | Blake et al. ...................... 222/207 |
| 4,231,724 | 11/1980 | Hope et al. ....................... 417/472 |
| 4,265,601 | 5/1981 | Mandroian ........................ 417/379 |
| 4,276,004 | 6/1981 | Hahn ................................ 417/479 |
| 4,282,867 | 8/1981 | Du Toit ........................... 128/66 |
| 4,299,221 | 11/1981 | Philips et al. .................. 128/276 |
| 4,325,368 | 4/1982 | Kaemmerer ...................... 128/124 R |
| 4,381,005 | 4/1983 | Bujan . |
| 4,457,753 | 7/1984 | Pastrone ........................... 604/153 |
| 4,569,674 | 2/1986 | Philips et al. .................. 604/119 |
| 4,621,566 | 11/1986 | Johnson et al. ................. 92/13.4 |
| 4,634,430 | 1/1987 | Polaschegg ...................... 604/141 |
| 4,655,690 | 4/1987 | Boedecker et al. ............. 417/53 |
| 4,655,754 | 4/1987 | Richmond et al. .............. 604/323 |
| 4,662,829 | 5/1987 | Nehring .......................... 417/395 |
| 4,732,549 | 3/1988 | von Schuckmann .............. 417/472 |
| 4,776,840 | 10/1988 | Freitas et al. .................. 604/33 |
| 4,826,494 | 5/1989 | Richmond et al. .............. 604/323 |
| 4,930,997 | 6/1990 | Bennett .......................... 417/410 |
| 4,995,864 | 2/1991 | Bartholomew et al. ......... 604/153 |
| 5,019,038 | 5/1991 | Linden ............................ 604/49 |
| 5,046,486 | 9/1991 | Grulke et al. .................. 128/66 |
| 5,097,540 | 3/1992 | Lovitt ............................. 4/443 |
| 5,193,986 | 3/1993 | Grant et al. .................... 417/98 |
| 5,195,959 | 3/1993 | Smith .............................. 604/34 |

(List continued on next page.)

FOREIGN PATENT DOCUMENTS

WO 9625188 8/1996 WIPO .

*Primary Examiner*—Michael A. Brown
*Attorney, Agent, or Firm*—Arthur Z. Bookstein; John F. Perullo

[57] ABSTRACT

A self-priming pulsatile surgical irrigation device is disclosed. The irrigation device comprises a housing, a variable volume pumping chamber liquid pump contained within the housing, and a self-priming valve system operatively associated with the liquid pump. The self-priming valve system, which facilitates the priming of the device, includes a valve housing, a liquid inlet to admit liquid into the valve housing and a liquid outlet to emit liquid from the housing. The housing is configured to define a flow path that directs liquid from the liquid inlet into the pumping chamber. The flow path ensures that the pumping chamber is maintained full during operation of the pump.

18 Claims, 3 Drawing Sheets

U.S. PATENT DOCUMENTS

| | | | |
|---|---|---|---|
| 5,207,697 | 5/1993 | Carusillo et al. | 606/167 |
| 5,230,704 | 7/1993 | Moberg et al. | 604/34 |
| 5,246,367 | 9/1993 | Ito et al. | 433/80 |
| 5,261,883 | 11/1993 | Hood et al. | 604/153 |
| 5,269,750 | 12/1993 | Grulke et al. | 604/21 |
| 5,281,108 | 1/1994 | Brooke | 417/395 |
| 5,282,787 | 2/1994 | Wortrich | 604/30 |
| 5,290,236 | 3/1994 | Mathewson | 604/131 |
| 5,322,506 | 6/1994 | Kullas | 604/153 X |
| 5,325,867 | 7/1994 | Skrabal et al. | 604/153 X |
| 5,335,855 | 8/1994 | Borod | 239/152 |
| 5,360,338 | 11/1994 | Waggoner | 433/80 |
| 5,368,569 | 11/1994 | Sanese | 604/113 |
| 5,470,305 | 11/1995 | Arnett et al. | 604/153 X |

SELF-PRIMING PULSED LAVAGE PUMP

FIELD OF THE INVENTION

This invention relates to a self-priming pulsed lavage device usable in a surgical environment to deliver irrigation liquid to a surgical site.

BACKGROUND OF THE INVENTION

It is important during a surgical procedure to maintain the operative site clean, antiseptic and free of debris. One common technique for maintaining a clean surgical site is to irrigate the site with an irrigation or antiseptic solution. Typically, the irrigation liquid is supplied from a reservoir through tubing to a dispensing handle that is manipulated by a physician or an assistant. Removal of the irrigation liquid, as well as other liquids that may collect at the surgical site, is effected by applying a suction instrument to the irrigated site.

A number of combination irrigation and suction devices have been used and proposed. Many incorporate an arrangement for delivering the liquid in a pulsatile manner to dislodge debris, and suctioning the irrigation liquid and other liquids that collect at the surgical site. One such pump is shown, for example, in co-pending patent application, "Pulsed Lavage Pump with Integral Power Source and Variable Flow Control" to Pasch et al. (Ser. No. 08/389,155, filed Feb. 15, 1995). The device generally includes tubing that is connectable directly to the reservoir by a spike at the end of the tubing. The other end of the tubing is connected to a handpiece. All of the components for pumping and controlling the liquid may be contained within the handpiece. The handpiece generally includes a housing that contains a variable volume chamber liquid pump, a trigger movably mounted to the housing to control the operation of the liquid pump, and a valve system operatively associated with and in direct liquid communication with the pump. The pump includes a reciprocating bellows pump that draws liquid from an external reservoir into a valve housing during a filling stroke and then ejects liquid from the valve housing in a pumping stroke. The housing has one-way inlet valve and a one-way outlet valve to control the direction of fluid flow. In order for the device to operate with maximum pumping efficiency, it is important that it be substantially fully primed, that is, that the bellows and the valve housing be filled substantially fully with the liquid. The pump system described in the above-identified application is best primed while the device is held in a specific orientation. There may be instances, however, when the user does not orient the device in the optimum priming attitude which may result in increased time to prime the device or insufficient priming. The insufficient priming may not correct itself during operation of the device. Consequently, the pumping efficiency of the device may be compromised.

It would be desirable to provide an entirely self-contained powered pulsatile irrigation device that can be primed quickly and independently of the attitude of the device.

SUMMARY OF THE INVENTION

The invention facilitates self-priming of the pump system in a pulsed lavage device independently of the orientation of the device. That is accomplished by providing a flow path within the valve housing that directs liquid from the one-way inlet valve directly to the mouth of the bellows thereby assuring that the bellows will fill completely. More particularly, the interior of the valve housing is formed to define a segmented flow path including a first segment that extends from the inlet valve to the mouth of the bellows, a second segment that includes the pumping chamber within the bellows and a third segment that extends from the mouth of the bellows to the outlet valve. The segments are defined by an internal baffle within the valve housing that precludes direct flow communication from the inlet valve to the outlet valve. Consequently, when the bellows is actuated by the reciprocating drive system, liquid drawn into the device will be directed into the bellows before liquid can flow to the outlet valve. Consequently, the bellows becomes substantially filled before the third segment of the flow path, from the mouth of the bellows to the outlet valve, becomes filled. When all three segments of the flow path are substantially filled, the priming process is complete and the device will deliver maximum liquid volume and maximum pressure to the surgical site. The invention avoids the necessity for orienting or manipulating the device to a specific attitude in order to effect full priming.

The bellows may be formed as a separate member placed in the valve chamber or it may be formed integrally with the valve chamber. The baffle is arranged to direct liquid along the first segment of the flow path into the mouth of the bellows, and is oriented so that it presents minimal obstruction to flow of liquid from the bellows to the third segment of the flow path during an ejection stroke.

It is therefore among the objects of the invention to provide a hand-held pulsatile surgical irrigation device having a self-priming pump system.

Another object of the invention is to provide a device of the type described in which the system is self-priming independently of the orientation in which the device is held.

A further object of the invention is to provide a hand-held, self-priming surgical irrigation device in which the liquid flow path includes a plurality of sequentially arranged segments.

Another object of the invention is to provide a device of the type described in which a valve chamber having inlet and outlet valves is separated into segments that preclude direct communication of the valves with each other.

DESCRIPTION OF THE DRAWINGS

The foregoing and other objects and advantages of the invention will be appreciated more fully from the following further description thereof, with reference to the accompanying drawings of which.

DESCRIPTION OF THE PREFERRED EMBODIMENT

The invention facilitates the priming of a pulsed lavage pump device that is a part of a larger irrigation system. In particular, it provides a flow pattern within the pumping system by which the pump is self-priming upon actuation of the pump.

Figure 1:
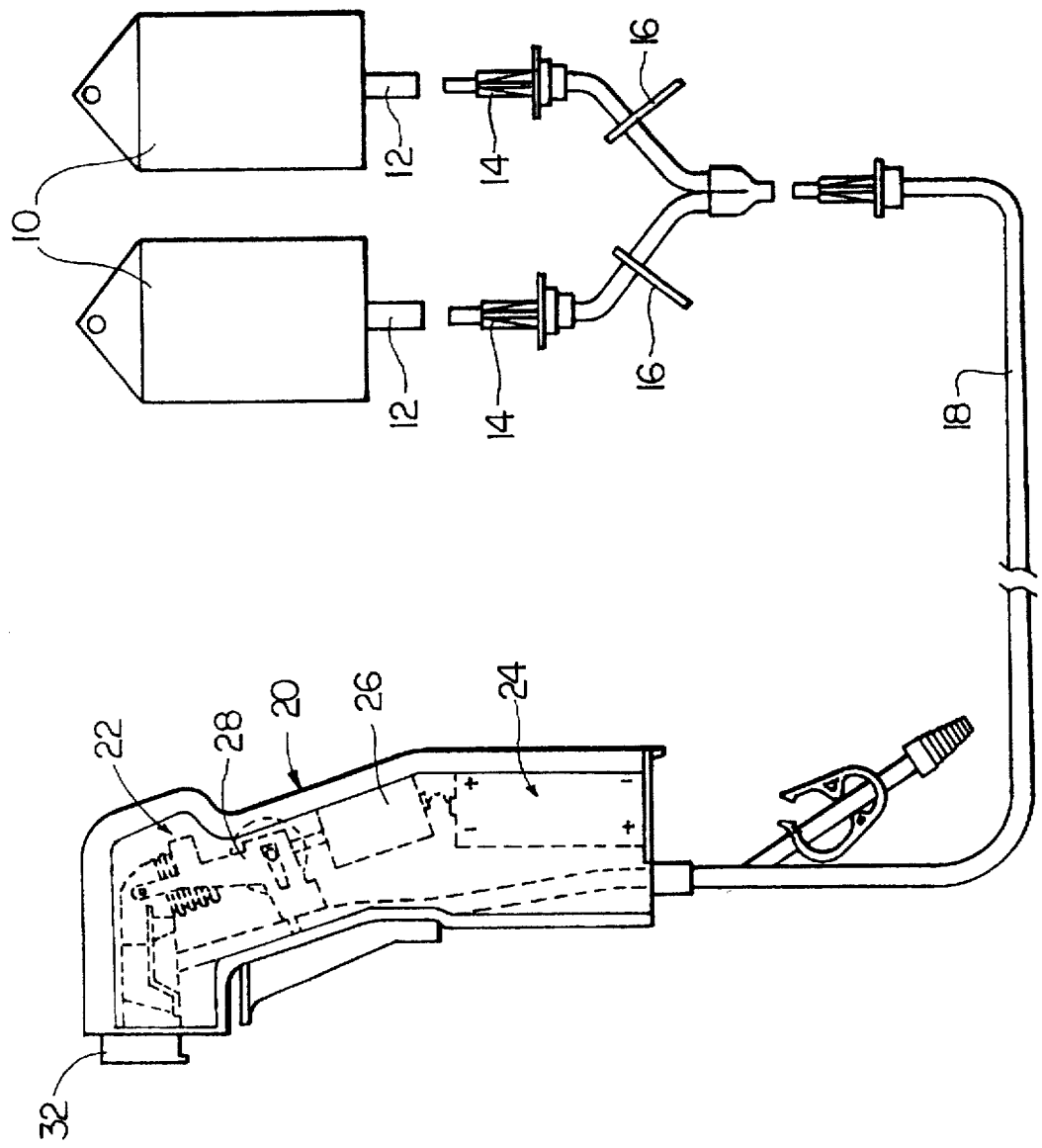
FIG. 1 is a schematic illustration of an irrigation system used in connection with the irrigation device with the internal handle components illustrated in phantom.

As shown in FIG. 1, the irrigation system includes a reservoir of irrigation liquid (e.g., saline), such as one or more bags 10 containing the liquid. The reservoir preferably is adapted to be suspended overhead, as from an I.V. pole, in order to create a gravity pressure head that can facilitate flow of liquid through the system. Each irrigation bag 10 has an outlet port 12 adapted to receive a spike adapter 14 on an end of the flexible tubing to connect the tubing to the irrigation bags 10. Clamps 16 may be provided at various locations along the tubing to control the flow through the tubing. The device includes a liquid delivery tube 18 that is connectable, at one end, either directly or indirectly to the irrigation bags 10 and, at the other end, to a handpiece 20.

Figure 2:
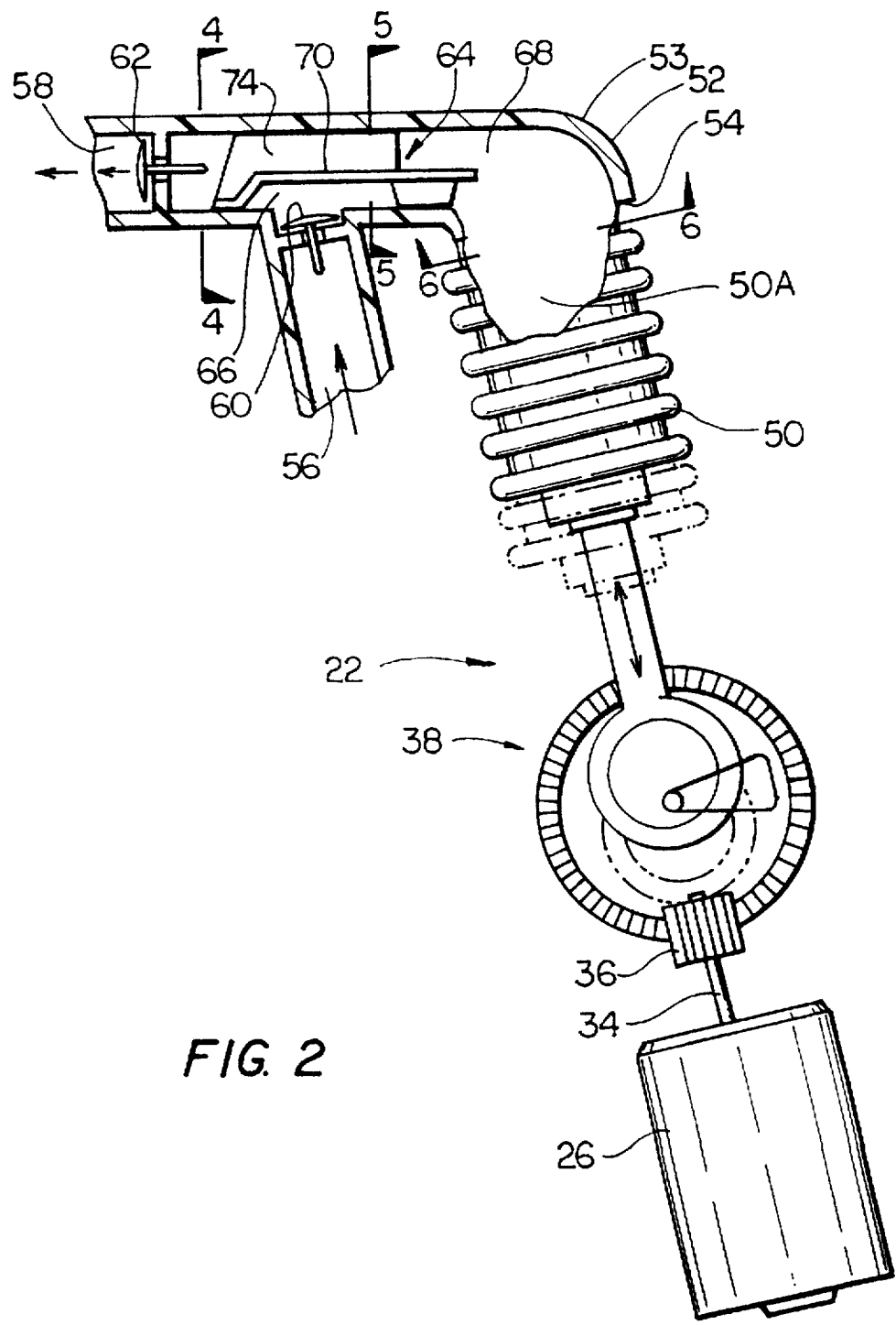
FIG. 2 is a somewhat schematic illustration, fragmented and in section, of the pumping mechanism and valve system in accordance with the invention.

The handpiece 20, which may be somewhat pistol-shaped, contains a self-powered pump system, the components of which are illustrated generally in phantom in FIG. 2. The contained components include a pump mechanism 22, a battery power source 24, a motor 26 and a control mechanism 28 that couples the motor 26 with the pump mechanism 22. A trigger 30 is movably mounted to the handpiece 20 so that when squeezed, it will close electrical contacts to initiate operation of the motor to drive the pump. Squeezing the trigger 30 also controls the control mechanism 28 by which the length of stroke of the pump, and, therefore, its output volume, can be varied. Progressive squeezing of the trigger 30 results in progressively increased flow of irrigation liquid. The operation of the device is described more fully in co-pending patent application Ser. No. 08/389,155 filed Feb. 15, 1995 (Pasch et al.), the disclosure of which is hereby incorporated, in its entirety, by reference.

FIG. 2 shows, somewhat diagrammatically, the pump mechanism 22 modified in accordance with the invention. The motor 26 includes an output shaft 34 that carries a pinion gear 36 that, in turn, drives a face gear 38. The face gear has an eccentric boss 40 that drives a connecting rod 42 in a reciprocating manner suggested by the arrow 44. The connecting rod 42 is secured to the free movable and variable volume pump element, such as a flexible bellows 50. Operation of the motor 26 thus reciprocates the bellows in alternating filling and pumping strokes.

The bellows 50 may be formed from any of a variety of materials including a variety of flexible polymers. One end of the bellows 50 is securely attached to a bellows port 54 of a valve housing 52, while the other end of the bellows is movable and attached to the reciprocating connecting rod 42.

The valve housing 52, which may be molded from any of a variety of moldable polymeric materials, is in direct liquid communication with the bellows 50 at bellows port 54. The bellows 50 defines a variable volume pumping chamber that can be filled with irrigation liquid through bellows port 54. The valve housing 52 also includes an inlet port 56 to admit liquid into the valve housing 52, and an outlet port 58 to emit liquid from the valve housing 52. Each of the ports 56 and 58 is provided with an umbrella valve, 60 and 62, respectively to effect one-way liquid flow through the valve housing 52. In accordance with the invention, the valve housing 52 is configured to define a flow path that directs liquid from the inlet port 56 into the bellows chamber so as to assure self-priming and full flow independent of the orientation of the device.

Figure 3:
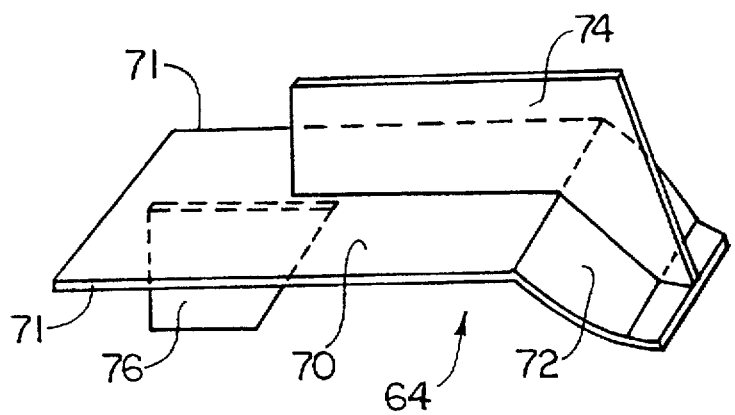
FIG. 3 is an enlarged asymmetric illustration of a baffle that may be placed in the valve housing illustrated in FIG. 2 to separate the valve housing so as to define the three flow path segments.
Figure 4:
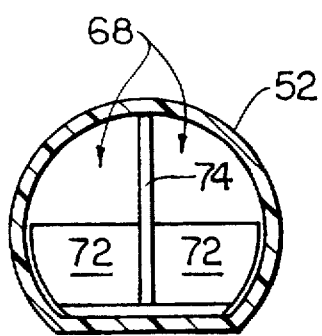
FIG. 4 is a somewhat diagrammatic sectional illustration of the device as seen along line 4—4 of FIG. 2.
Figure 5:
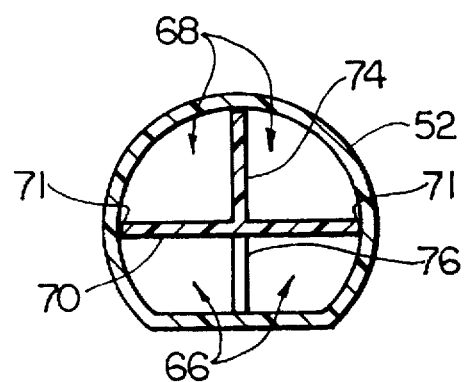
FIG. 5 is a somewhat sectional diagrammatic illustration of the device as seen along line 5—5 of FIG. 2.

The flow path through the valve housing 52 and bellows 50 may be considered as having three segments including a first segment 66 that extends between the inlet port 56 and the mouth of the bellows 50, a second segment that includes the bellows chamber itself and a third segment 68 that extends from the mouth of the bellows to the outlet port 58. The segments are defined by a baffle 64 that forms a wall 70 between the first and third segments 66 and 68. In the illustrative embodiment of the invention, the baffle 64 may take the form of an insert that can fit within the generally tubular valve housing 52 to define the flow lumen of the valve housing into the first and third chambers 66 and 68. FIG. 3 illustrates such a baffle 64, its position within the valve housing 52 being illustrated in FIG. 2. The segments of the flow path are illustrated in FIG. 2 as including the first segment 66 and the third segment 68. The second segment comprises the interior chamber of the bellows (bellows chamber 50A).

The divider wall 70 of the baffle spans the width of the valve housing 52 and has lateral edges 71 that engage the inner surface of the valve housing. The baffle 64 also includes an end wall 72 that mates with the inner contour of the valve housing to close off the first segment 66 of the flow path from the outlet port 58. The baffle 64 also may include an upper stabilizer fin 74 and a lower stabilizer fin 76 that engage other portions of the inner surface of the valve housing to stabilize the position of the baffle 64. Thus, the wall 70 of the baffle 64 divides the valve housing 52 to define a flow path having a first segment 66 that is in communication with the inlet port 56, a second segment that comprises the bellows chamber and a third segment 68 that is in communication with the outlet port 58. The inlet port 56 and outlet port 58 are not in direct liquid communication with each other.

Figure 6:
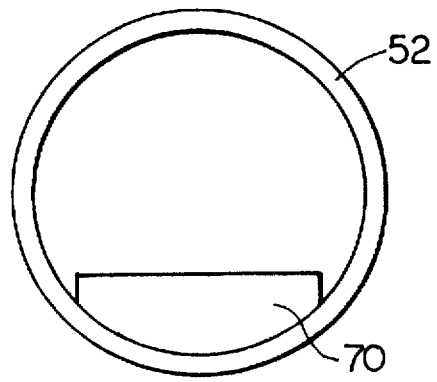
FIG. 6 is a somewhat diagrammatic illustration of the device as seen along line 6—6 of FIG. 2.

As shown in FIGS. 2 and 6, the valve housing 52 has a shoulder 53 that defines the bellows port 54 to which the mouth of the bellows is secured. The baffle wall 70 is positioned to extend only to assure that liquid will be directed to the bellows but not so much as to obstruct the bellows port 54, thereby facilitating the free flow of liquid from the bellows chamber 50A into the third segment 68 during the pumping stroke when the device is operating. Such positioning therefore enables the baffle 64 to direct a maximum amount of liquid into the bellows chamber 50A while not inhibiting the flow of liquid from the bellows chamber 50A into the third segment 68 of the flow path.

During priming, the pumping action of the bellows 50 creates an aspiration through the flexible tube 18 that causes liquid to flow from the reservoir 10 and into the first segment 66 through the inlet umbrella valve 60. Since the liquid is flowing under pressure, the baffle 64 directs the liquid into the bellows chamber 50A regardless of the orientation of the pump 40. No significant amounts of liquid enter the third segment 68 until the bellows chamber 50A is substantially filled with liquid. Accordingly, the baffle 64 ensures that during priming of the pump, the bellows chamber 50A will be filed before the third segment 68 fills, and, depending upon the orientation of the device, it may fill before the first segment 66 fills.

It has been experimentally determined that the pump will typically prime within two to three seconds when the handpiece 20 is oriented so that the nozzle 32 is pointing upwardly or in a horizontal direction. It has also been experimentally determined that the pump will still prime while the handpiece 20 is oriented so that the nozzle 32 is pointing downwardly. When in this orientation, however, the pump typically takes on the order of about two to three seconds longer to prime because the bellows chamber is at the highest vertical point in the valve housing 52 and is somewhat inverted. The configuration of the valve housing 52 nevertheless ensures that the bellows chamber 50A will still be filled prior to the third segment 68. Accordingly, the invention enables an expandable chamber pump to self-prime between approximately two to six seconds in any orientation.

When the pump is fully primed, (i.e. when the two segments and bellows chamber 50A are substantially filled), as the bellows 50 is reciprocated, the expansion portion of its stroke will cause irrigation liquid to be sequentially drawn through the liquid delivery tube 18, the inlet umbrella valve 60, the first segment 66, the bellows chamber 50A, and into the second segment 68. When the stroke of the bellows 50 reverses, in a pumping direction, liquid contained within the valve segments 66 and 68 and bellows chamber 50A will be ejected through the outlet port 58, past the umbrella valve 62. Continued reciprocation of the bellows 50 will cause repeated pulsating flow through the system and out of the irrigation line of the handpiece 20.

From the foregoing, it should be appreciated that the invention provides a self-priming pulsating irrigation device for use in surgical and other medical environments where pulsed lavage is desirable. A user is therefore able to easily prime the pump without having to manipulate the orientation of the pump. Accordingly, the volume and pressure of liquid emitted during each pulsing cycle is more easily maximized without requiring the user to be inconvenienced by having to specially orient the device. It should also be appreciated that the device may include each of the elements disclosed in the Pasch et al. patent application.

It should be understood, however, that the foregoing description of the invention is intended merely to be illustrative thereof and that other embodiments, modifications and equivalents may be apparent to those skilled in the art without departing from its spirit.

Having thus described the invention what we desire to claim and secure by Letters Patent is:

1. A self-priming pulsatile surgical irrigation device comprising:

a housing;

a liquid pump contained within the housing and having a variable volume pumping chamber open to a port at one end; and a self-priming valve system operatively associated with the liquid pump to effect priming of the pump, the valve system comprising a valve housing in direct liquid communication with the pumping chamber, a liquid inlet to accept liquid into the valve housing, and a liquid outlet to emit liquid from the valve housing;

the valve housing and pumping chamber being configured to define a flow path having a first segment in communication with the liquid inlet, a second segment comprising the pumping chamber, and a third segment in communication with the liquid outlet and the flow path being configured to sequentially direct liquid from the first segment through the port into the second segment in the pumping chamber, and then back through the port to the third segment during operation of the pump.

2. The device as defined in claim 1 wherein the configuration of the flow path is such as to cause the pumping chamber to be filled before the valve housing is filled.

3. A device as defined in claim 1 wherein the valve housing further comprises a baffle that defines at least part of the flow path.

4. The device as defined in claim 3 wherein the baffle comprises a unitary member having fins extending therefrom to secure the baffle within the valve housing.

5. A device as defined in claim 3 wherein the pumping chamber is defined by a bellows.

6. The device as defined in claim 3 wherein the baffle is positioned to cause the pumping chamber to fill before the third segment is filled.

7. The device as defined in claim 3 wherein the baffle is positioned to facilitate free flow of liquid from the pumping chamber into the third segment.

8. The device as defined in claim 1 further comprising a means mounted to the housing for controlling the operation of the liquid pump.

9. The device as defined in claim 1 wherein the liquid inlet is positioned upstream of the pumping chamber and liquid outlet is positioned downstream of the pumping chamber.

10. A self-priming valve system operatively associated with a pump having a variable volume pumping chamber open to a port at one end, the valve system comprising:

a valve housing in direct liquid communication with the pumping chamber;

a liquid inlet to accept liquid into the valve housing; and a liquid outlet to emit liquid from the valve housing;

the valve housing and pumping chamber being configured to define a flow path having a first segment in communication with the liquid inlet, a second segment comprising the pumping chamber, and a third segment in communication with the liquid outlet and the flow path being configured to sequentially direct liquid from the first segment through the port into the second segment in the pumping chamber, and then back through the port to the third segment during operation of the pump.

11. The valve system as defined in claim 10 wherein the configuration of the flow path is such as to cause the pumping chamber to be filled before the valve housing is filled.

12. The valve system as defined in claim 10 wherein the valve housing further comprises a baffle that defines at least part of the flow path.

13. The valve system as defined in claim 12 wherein the baffle is positioned to cause the pumping chamber to be filled before the third segment is filled.

14. The valve system as defined in claim 12 wherein the baffle comprises a unitary member having fins extending therefrom to secure the baffle within the valve housing.

15. The valve system as defined in claim 12 wherein the baffle is positioned to facilitate free flow of liquid from the pumping chamber into the third segment.

16. The valve system as defined in claim 10 further comprising:

a first one-way valve to effect liquid flow into the valve housing from the liquid inlet; and a second one-way valve to effect liquid flow out of the valve housing and towards the liquid outlet.

17. The valve system as defined in claim 10 wherein the pumping chamber is defined by a bellows.

18. The valve system as defined in claim 10 wherein the liquid inlet is positioned upstream of the pumping chamber and the liquid outlet is positioned downstream of the pumping chamber.

* * * * *